(12) United States Patent
Honebrink

(10) Patent No.: US 7,029,468 B2
(45) Date of Patent: Apr. 18, 2006

(54) CATHETER ASSEMBLY WITH SIDE WALL EXIT LUMEN AND METHOD THEREFOR

(75) Inventor: Brian Honebrink, Stillwater, MN (US)

(73) Assignee: Enpath Medical, Inc., Minneapolis, MN (US)

( * ) Notice: Subject to any disclaimer, the term of this patent is extended or adjusted under 35 U.S.C. 154(b) by 215 days.

(21) Appl. No.: 10/179,124

(22) Filed: Jun. 25, 2002

(65) Prior Publication Data
US 2003/0236492 A1   Dec. 25, 2003

(51) Int. Cl.
A61M 25/00   (2006.01)
A61M 5/00    (2006.01)
A61M 37/00   (2006.01)

(52) U.S. Cl. ............... 604/528; 604/525; 604/103.05; 604/95.01; 600/434

(58) Field of Classification Search ........ 604/500–524, 604/95.04, 195.01, 102.02; 600/434, 467; 606/194
See application file for complete search history.

(56) References Cited

U.S. PATENT DOCUMENTS

| | | | |
|---|---|---|---|
| 4,033,331 A * | 7/1977 | Guss et al. ............... | 600/434 |
| 4,149,535 A * | 4/1979 | Volder .................... | 604/43 |
| 4,898,577 A | 2/1990 | Badger et al. ............ | 604/53 |
| 5,219,335 A * | 6/1993 | Willard et al. .......... | 604/103.05 |
| 5,391,146 A | 2/1995 | That et al. ............. | 604/95 |
| 5,429,604 A | 7/1995 | Hammersmark et al. .... | 604/95 |
| 5,642,736 A | 7/1997 | Avitall ................. | 128/772 |
| 5,964,757 A | 10/1999 | Ponzi ................... | 606/45 |
| 6,171,277 B1 | 1/2001 | Ponzi et al. ........... | 604/95.04 |
| 6,251,092 B1 | 6/2001 | Qin et al. ............. | 604/95.01 |
| 6,273,879 B1 * | 8/2001 | Keith et al. ........... | 604/523 |
| 6,309,379 B1 * | 10/2001 | Willard et al. ......... | 600/467 |
| 6,485,457 B1 * | 11/2002 | Hisamatsu et al. ...... | 604/102.02 |
| 6,746,442 B1 * | 6/2004 | Agro et al. ............ | 604/523 |
| 2001/0049491 A1 | 12/2001 | Shimada ................ | 604/95.04 |

FOREIGN PATENT DOCUMENTS

WO   WO-02/15972   2/2002

* cited by examiner

Primary Examiner—Nicholas D. Lucchesi
Assistant Examiner—Roz Maiorino
(74) Attorney, Agent, or Firm—Schwegman, Lundberg, Woessner & Kluth, P.A.

(57) ABSTRACT

A catheter assembly includes a catheter body that extends from a distal end to a proximal end. The catheter body includes a delivery lumen, and an actuator lumen, where the actuator lumen extends from a position near or at the distal end to an intermediate portion that does not extend through the proximal end of the catheter body. The catheter body optionally includes an accessory lumen that extends from at or near the distal end and terminates at an intermediate portion that does not extend through the proximal end surface of the catheter body, for example, on a side wall.

14 Claims, 6 Drawing Sheets

CATHETER ASSEMBLY WITH SIDE WALL EXIT LUMEN AND METHOD THEREFOR

TECHNICAL FIELD

The present invention relates generally to a deflectable catheter assembly. More particularly, it pertains to a pull wire assembly for a deflectable catheter assembly.

BACKGROUND

Increase in the use of stents, leads, and ablation techniques in branch vessels has provided an increased demand on the placement techniques for these devices. For some procedures, it is necessary to initially position a guidewire into a desired part of the lumen of a desired vessel or duct, such as a blood vessel. After the guidewire is positioned within the desired location, a catheter or other tubular device may be positioned over the guidewire and used to convey other medical instruments into the desired blood vessel or duct.

Alternatively, a guiding catheter is used to negotiate the vasculature of a patient. One example of a guiding catheter is described in U.S. Pat. No. 4,898,577 to Badger et al. The Badger guiding catheter includes a single elongate shaft that has a deflectable distal portion controllable by a pull wire. Once the distal portion is at the required deflection or location within the patient, the guidewire or medical instrument is fed through a delivery lumen of the catheter.

The deflectable catheter is controlled at a proximal end of the catheter by a control handle that operates a pull wire to deflect the catheter, for example, as shown in U.S. Pat. No. 6,171,277. In many conventional catheters, the pull wire is disposed within a pull wire lumen, where the pull wire lumen extends from the distal portion of the shaft through an opening at the proximal end surface of the shaft. The pull wire opening at the proximal end surface is directly adjacent to a delivery lumen that extends from the distal end through the proximal end surface, which has several drawbacks. For instance, blood which enters the delivery lumen at the distal end can travel to the proximal end of the shaft and enter the pull wire lumen, potentially resulting in contamination issues. Another potential drawback is when the blood entering the pull wire lumen clots within the pull wire lumen or around the pull wire, the operation of the pull wire is impeded, rendering it difficult to manipulate the distal end of the shaft. Another potential drawback with this pull wire lumen and delivery lumen is the risk of embolism.

Accordingly, what is needed is a deflectable catheter that overcomes the shortcomings of previous deflectable catheters. What is further needed is a deflectable catheter that allows for more accurate positioning of the distal end of the deflectable catheter.

SUMMARY

A deflectable catheter assembly includes a catheter body extending from a deflectable distal end to a proximal end and having an intermediate portion therebetween. The catheter body includes an actuator lumen and a delivery lumen, where the delivery lumen extends from the deflectable distal end through the proximal end. The actuator lumen extends from a position near the deflectable distal end to the intermediate portion, but not through the proximal end, and forming an exit lumen in a side wall of the catheter body.

Several options for the deflectable catheter assembly are as follows. For instance, in one option, the assembly further includes a pull wire disposed within the actuator lumen, where the pull wire is coupled with the catheter body near the deflectable distal end, and optionally exits through the exit lumen. In yet another option, the assembly further includes a liner disposed within the actuator lumen and/or the delivery lumen. A further option includes coupling or embedding a stiffening member with the liner. Still further, in another option, the assembly further includes a means for deflecting the deflectable distal end. In yet another option, a means for sealing the actuator lumen is provided.

In another embodiment, a method includes forming a delivery lumen within a deflectable catheter assembly having a catheter body extending from a proximal end to a distal end. The method further includes forming a continuous actuator lumen along only a portion of the catheter body, and not forming a continuous actuator lumen through the distal end of the catheter body. The method further includes disposing a pull wire within the actuator lumen, and removing a portion of the pull wire from the actuator lumen through an exit lumen in a sidewall of the catheter body, the exit lumen continuous with the actuator lumen.

Several options for the method are as follows. For instance, in one option, the method further includes disposing a medical instrument through the delivery lumen and through the distal end of the catheter body. In yet another option, the method further includes placing a liner within the delivery lumen and/or the actuator lumen.

In another embodiment, a catheter assembly has a catheter body extending from a proximal end to a distal end and having a proximal tip and a distal tip. The catheter body further includes a side wall extending between the proximal end and the distal end, a delivery lumen, and an accessory lumen. The delivery lumen is sized to receive instruments therethrough, and the delivery lumen extends from proximal tip through the distal tip. The accessory lumen extends from the distal tip and terminates in the side wall of the catheter body, where the accessory lumen does not continuously extend from the distal tip to the proximal tip.

Several options for the catheter assembly are as follows. For instance, in one option, the catheter assembly further includes an actuator lumen extending from a location near the distal end and terminating in the side wall, where the actuator lumen does not extend through the proximal tip. In another option, the catheter is slittable without damage to an instrument disposed within the delivery lumen. In yet another option, the catheter assembly further includes a liner disposed within the accessory lumen. The catheter assembly further includes, in another option, an instrument disposed within the accessory lumen, such as a sensor, or a fiber optic assembly.

The deflectable catheter assembly provides a catheter assembly that is easy to use and manipulate, and does not interfere with the physician's ability to manipulate the deflectable catheter assembly. Furthermore, the catheter assembly design assists in preventing air leakage from the actuator lumen. The catheter assembly further prevents co-mingling of fluids from the delivery lumen to the actuator lumen, and prevents fluids from entering the actuator lumen and/or the accessory lumen.

These and other embodiments, aspects, advantages, and features of the present invention will be set forth in part in the description which follows, and in part will become apparent to those skilled in the art by reference to the following description of the invention and referenced drawings or by practice of the invention. The aspects, advantages, and features of the invention are realized and attained by means of the instrumentalities, procedures, and combinations particularly pointed out in the appended claims and their equivalents.

DESCRIPTION OF THE EMBODIMENTS

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that other embodiments may be utilized and that structural changes may be made without departing from the scope of the present invention. Therefore, the following detailed description is not to be taken in a limiting sense, and the scope of the subject matter of this application is defined by the appended claims and their equivalents.

FIGS. 1A and 1B illustrate a deflectable catheter assembly 100, where FIG. 1A illustrates the deflectable catheter assembly 100 in an articulated position, and FIG. 1B illustrates the deflectable catheter assembly 100 in an unarticulated position. The deflectable catheter assembly 100 includes a deflectable catheter body 110 and a handle assembly 150 that houses steering mechanisms for deflection of the catheter body 110. The handle assembly 150 allows for the deflection of a distal end of the catheter body 110. One example of the handle assembly 150 is described in co-pending application Ser. No. 10/179,633, assigned to Enpath Medical, Inc., and is entitled "Articulating Handle For a Deflectable Catheter," which is incorporated herein by reference. In one option, the pull wire 120 is connected to an actuator that is slid or rotated to apply tension to the pull wire 120. As tension is applied to the pull wire 120, the pull wire anchor at the distal end of the catheter body 110 is pulled causing the distal portion of the catheter body 110 to curve in a predetermined direction or directions.

Figure 1:
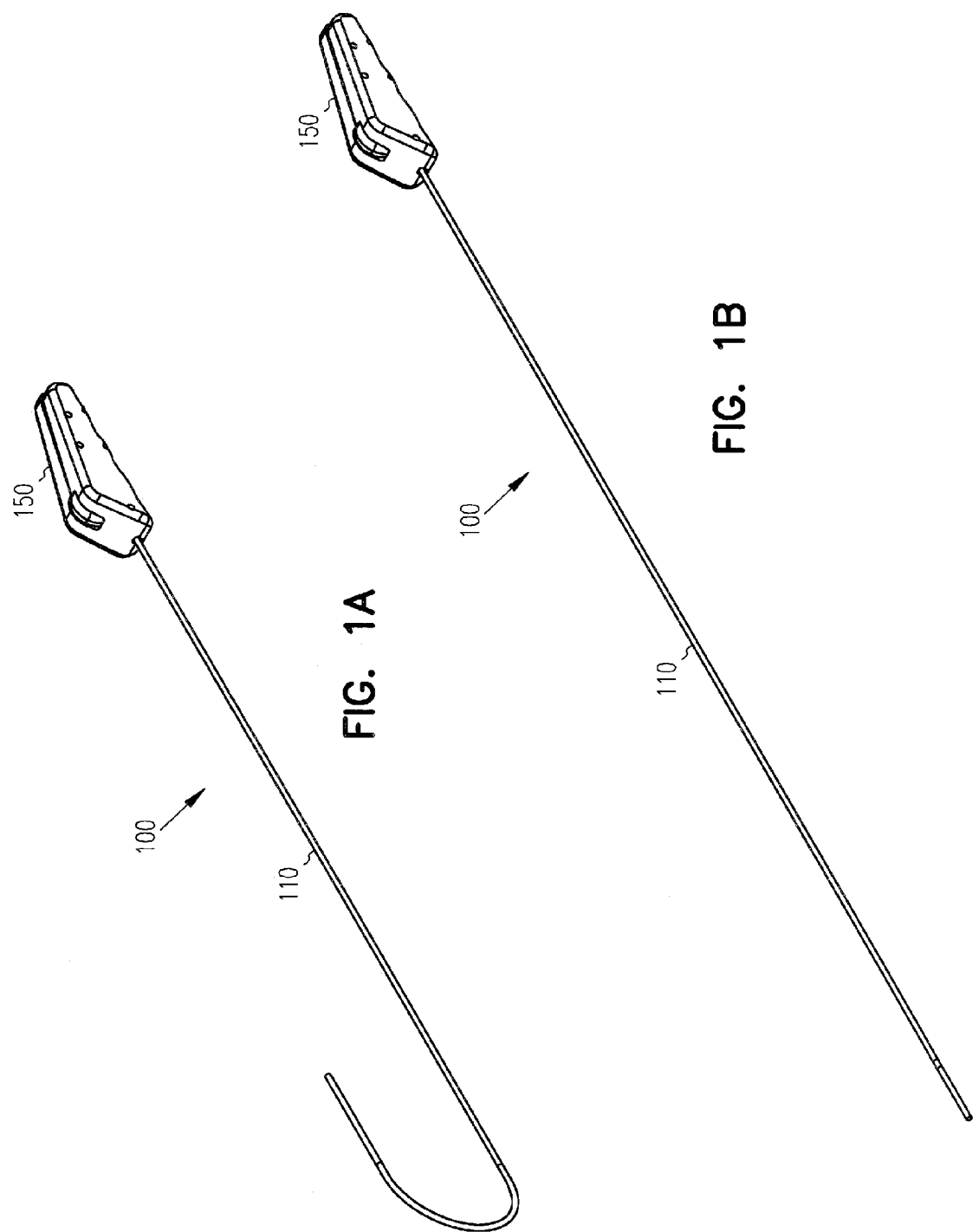
FIG. 1A is a perspective view illustrating a deflectable catheter assembly constructed in accordance with one embodiment.
FIG. 1B is a perspective view illustrating a deflectable catheter assembly constructed in accordance with one embodiment.
Figure 2:
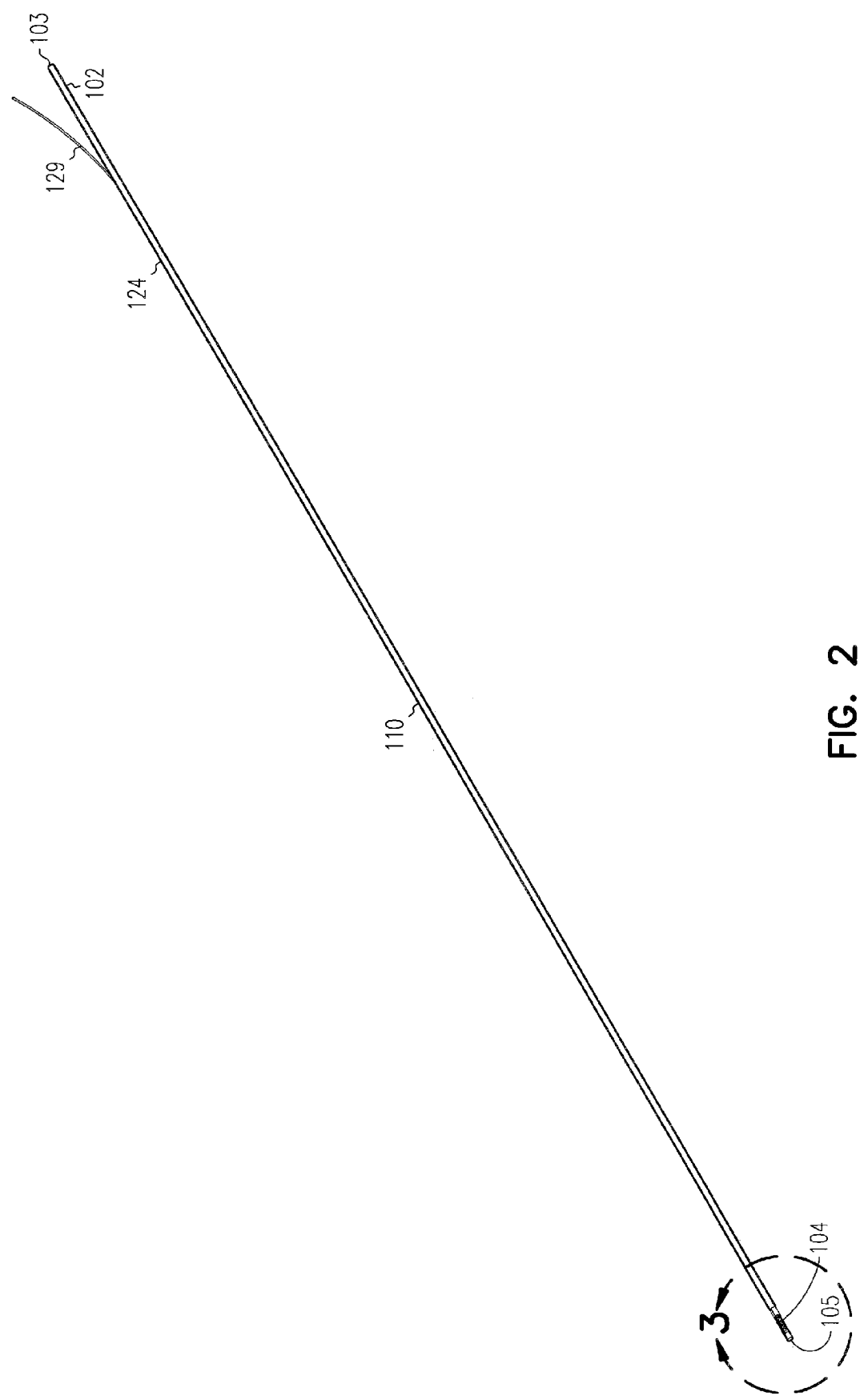
FIG. 2 is a perspective view illustrating a deflectable catheter body constructed in accordance with one embodiment.

With reference to FIG. 2, the catheter body 110 comprises an elongate tubular construction that is flexible yet substantially non-compressible along its length. The deflectable catheter body 110 extends from a proximal end 102 to a distal end 104, where the distal end 104 is disposed within a patient. At the proximal end 102 is a proximal tip 103, and at the distal end 104 is a distal tip 105. At the proximal end 102, the physician controls the deflection of the deflectable catheter body 110 with the handle assembly 150 (FIGS. 1A and 1B) and a pull wire 120 (FIG. 3), as further described below. The distal end 104 is deflected to traverse various branch vessels with the catheter assembly 100 (FIG. 1).

Figure 3:
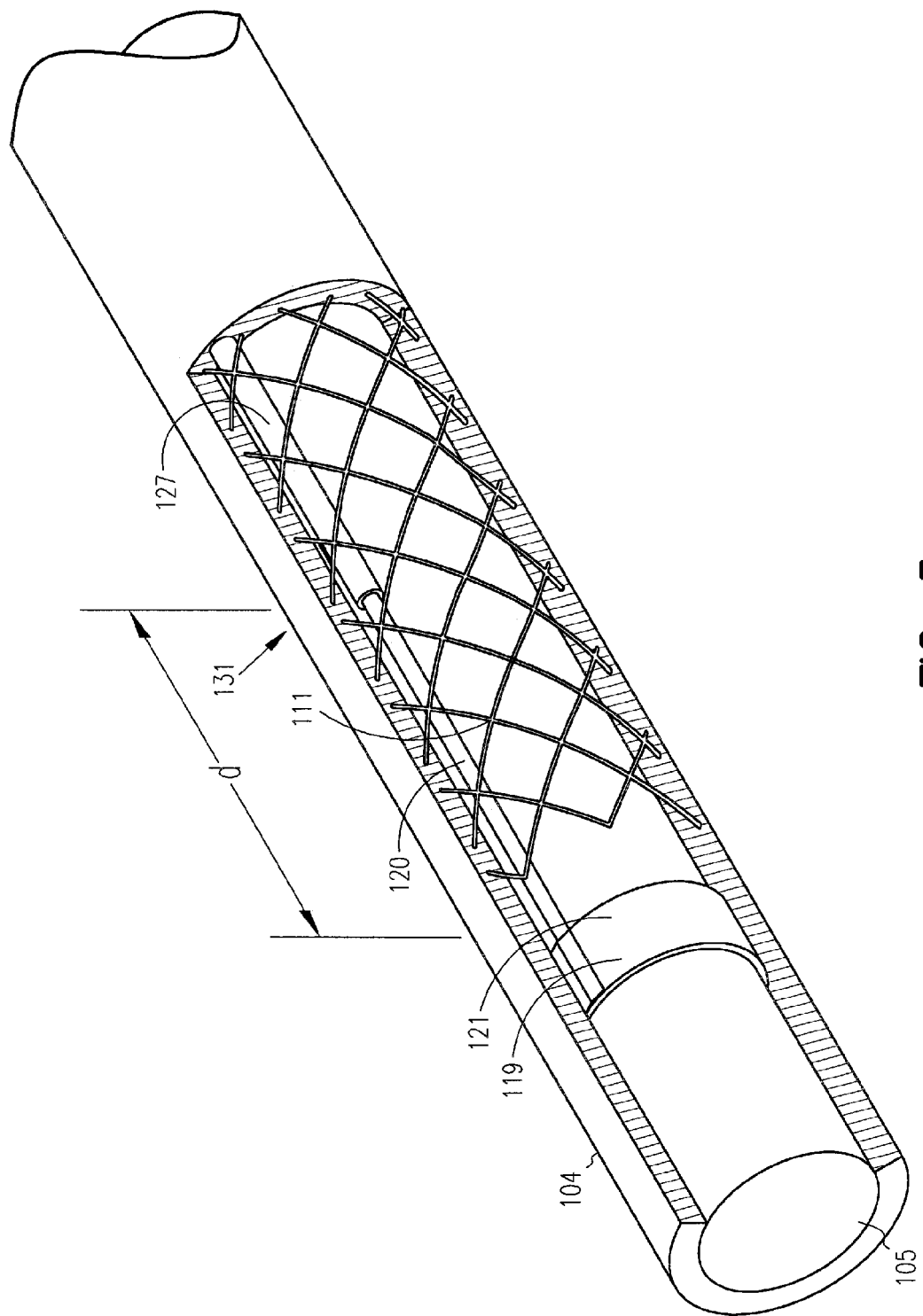
FIG. 3 is a perspective view illustrating a distal portion of the deflectable catheter body constructed in accordance with one embodiment.

FIG. 3 illustrates a partial cut-away view of FIG. 2, including the distal end 104 of the catheter body 110. The catheter body 110 includes a pull wire anchor 121 that is secured to the catheter body 110. The pull wire 120 is secured to the pull wire anchor 121, for example, as described in co-pending U.S. Provisional Patent Application entitled "Pull Wire Anchor For A Removable Medical Device And A Method Therefor," assigned to Enpath Medical, Inc., and having Ser. No. 60/409,494, which is incorporated herein by reference. It should be noted that the pull wire can be secured to the distal end 104 of the catheter body 110 in other manners. The pull wire anchor 121, in one option, comprises a marker band 119 that is viewable, for example, under fluoroscopy. In one option, the catheter body 110 includes a stiffening member embedded therein, such as a braided stainless steel member 111. The stiffening member facilitates rotation of the distal end 104 from the proximal end 102, and also assists in preventing the catheter body 110 from collapsing.

Figure 4:
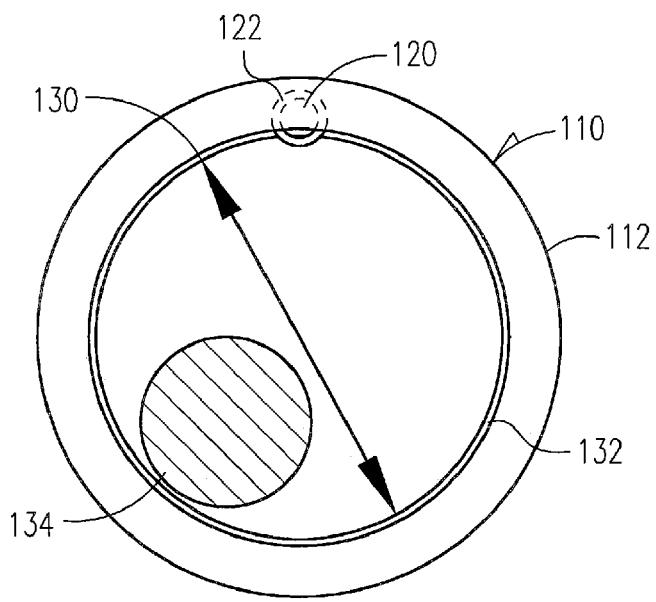
FIG. 4 is an end view of the distal end of the deflectable catheter assembly constructed in accordance with one embodiment.

FIG. 4 illustrates an end-view of the catheter body 110 at its, distal end 104 (FIG. 2). The catheter body 110 is further defined by an outer shaft surface 112. Disposed within the deflectable catheter body 110 includes at least one delivery lumen 130 that extends from the proximal end through the catheter body distal end 104. In one option, the delivery lumen 130 is lined with liner material 132, for example, PTFE. The lining of the delivery lumen 130 allows for instruments to be more easily inserted therethrough.

The delivery lumen 130 provides a passage from the controlling end to the distal end, such that a physician can insert a device or fluid in at the proximal end and it will travel through the catheter body 110 to the distal end 104 (FIG. 2), where it will exit the catheter body 110. The deflectable nature, of the body 110, in conjunction with the steering assembly, allows for a physician to direct the application of a device and/or medicine or fluid to a particular location within a patient. The delivery lumen 130 is configured to receive a variety of medical devices 134 therethrough. For example, suitable devices include, but are not limited to, leads, stents, dilators, guidewires, EP mapping catheters, ablation devices, etc. Alternatively, fluids and/or medicine can be distributed and targeted to a certain location using the deflectable catheter assembly 100 (FIG. 1A).

Figure 5:
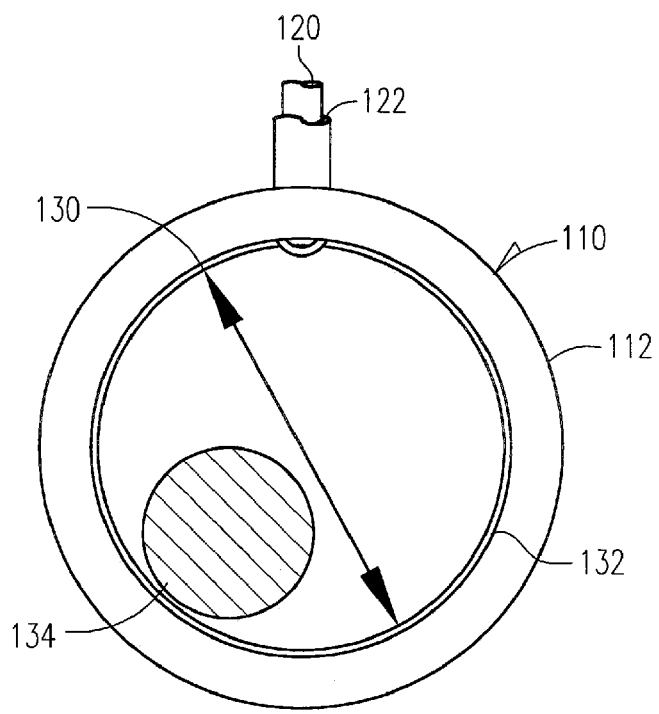
FIG. 5 is an end view of the proximal end of the deflectable catheter assembly constructed in accordance with one embodiment.

As mentioned above, the deflectable catheter assembly 100 (FIG. 1A) further includes a pull wire 120 associated therewith, where the pull wire 120 is received within an actuator lumen 122. The actuator lumen 122 is disposed within the catheter body 110, and the pull wire 120 is movably disposed within the actuator lumen 122. The actuator lumen 122 extends from a location near or at the distal end 104 (see FIG. 3) to an intermediate location that does not extend through the proximal end 102 (see FIG. 2). For example, the actuator lumen 122 terminates at a location in a side wall 124 of the catheter body 110. FIG. 5 illustrates an end view of the catheter body 110 at the proximal end. The lumen 122 does not extend to the proximal end nor to the proximal tip of the catheter body 110. Therefore, there is no cross-contamination of fluids or gasses from the delivery lumen 130 to the actuator lumen 122, or vice versa.

In one option, the actuator lumen 122 further includes an actuator lumen liner 126 therein. The actuator lumen liner 126 forms a lumen therein, where the lumen receives the pull wire 120 therein. The actuator lumen liner 126 is formed of PTFE in one option. Other suitable materials for the actuator lumen liner 126 include, but are not limited to, FEP or polyether-block-amide.

In yet another option, the actuator lumen liner 126 further includes a stiffening member such as braided material. The braided material assists in preventing the actuator lumen liner 126 from collapsing when the actuator lumen liner 126 is pulled out a side lumen, as further described below.

As shown in FIG. 3, the actuator lumen liner 126 extends from a location 131 near the distal end 104. In one option, the distal end 127 of the actuator lumen liner 126 is spaced away from the anchor 121 a distance "d". This allows for improved manufacturability of the catheter body 110 assembly. For instance, if the pull wire is not perfectly aligned with the pull wire anchor 121, this can result in irregularities in the outer diameter if the actuator lumen liner 126 extends up to the anchor 121.

Figure 6:
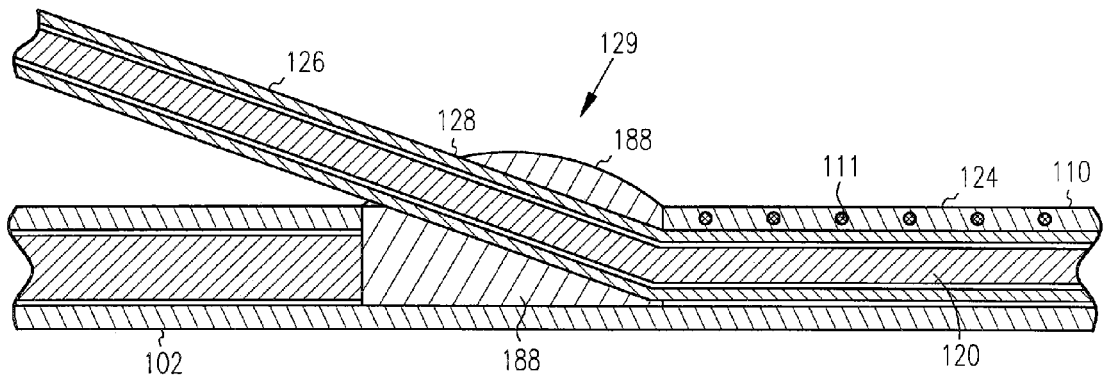
FIG. 6 is a cross-sectional view illustrating a portion of the deflectable catheter assembly constructed in accordance with one embodiment.

The actuator lumen liner 126 extends along the catheter body 110 to a location near the proximal end 102, as shown in FIG. 6. The actuator liner 126 exits through a side wall 124 of the catheter body 110 at 129. For example, in one option, the actuator lumen liner 126 is pulled through the side wall 124 of the catheter body 110 through an exit lumen 128 of the catheter body 110. The actuator lumen liner 126 does not continue within the catheter body 110 through the proximal end 102, and does not continue through the proximal tip of the catheter body 110. The actuator lumen liner 126 assists in sealing the proximal end of the catheter body 110, which prevents fluids exiting or co-mingling at the proximal end of the catheter body 110. In one option, a seal is formed around the actuator lumen liner 126 with material 188 reflowed around a portion of the actuator lumen liner 126.

Figure 7:
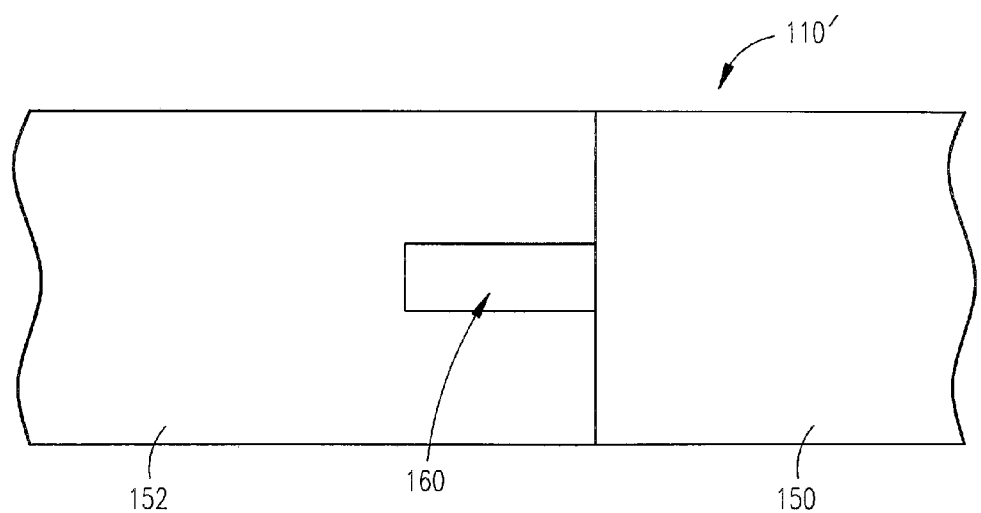
FIG. 7 is a side view illustrating a portion of a catheter body constructed in accordance with another embodiment.

FIG. 7 illustrates another option for the catheter body 110'. The catheter body 110' includes at least a first segment 150 and a second segment 152. In one option, the first segment 150 has a different durometer than the second segment 152. The first segment 150 is formed separate from the second segment, and the first segment includes a delivery lumen and an actuator lumen therein, as discussed above. The second segment 152 includes a delivery lumen, as discussed above. However, there are no lumens in the second segment 152 which are coupled with the actuator lumen. In one embodiment, the second segment 152 forms the proximal end of the catheter body 110', and the first segment 150 forms the intermediate portion of the catheter body 110'. In another option, a third segment having a different structure forms the distal end of the catheter body 110'. It should be noted that more segments are further options.

In yet another option, the catheter body 110' includes a notch 160 in the second segment 152 at a location 154 adjacent the first segment 150. The notch 160 allows for the actuator lumen liner (discussed above) to transition and exit more easily from an interior portion of the first segment 150, where the lumen and/or the liner do not extend through the proximal end surface of the catheter body 110'. The stress on the actuator lumen liner is reduced, and a smoother transition occurs.

To form the catheter assembly, in one example, the delivery lumen liner is placed over a mandrel, and the actuator lumen liner is threaded over the pull wire and placed over the delivery lumen liner. The pull wire anchor is placed over the delivery lumen liner and coupled with the pull wire. Stiffening material is optionally placed over the delivery lumen liner and the actuator lumen liner. Outer tubing is placed over the delivery lumen liner, which will form the outer surface of the catheter body. The items are held together, for example, by placing shrink tubing thereover and heating the shrink tubing. The items are reflowed together, a process which blends the material of the outer tubing, actuator lumen liner, and the delivery lumen liner. The shrink tubing is removed from the assembly.

To form the proximal end, an outer jacket is slid over a proximal end of the delivery lumen liner, but not over the actuator lumen liner. The outer jacket abuts the first outer jacket discussed above, and the items are secured together, for example, by heat shrink tubing. These elements are reflowed together, and the shrink tubing is removed. The deflectable catheter body assembly is coupled with a handle assembly with a steering mechanism to form the deflectable catheter assembly.

Figure 8:
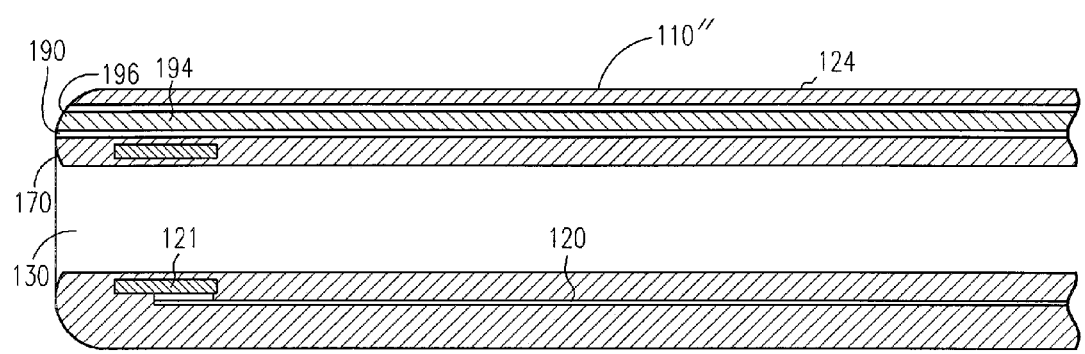
FIG. 8 is a cross-sectional view illustrating a distal end portion of a catheter body constructed in accordance with another embodiment.
Figure 9:
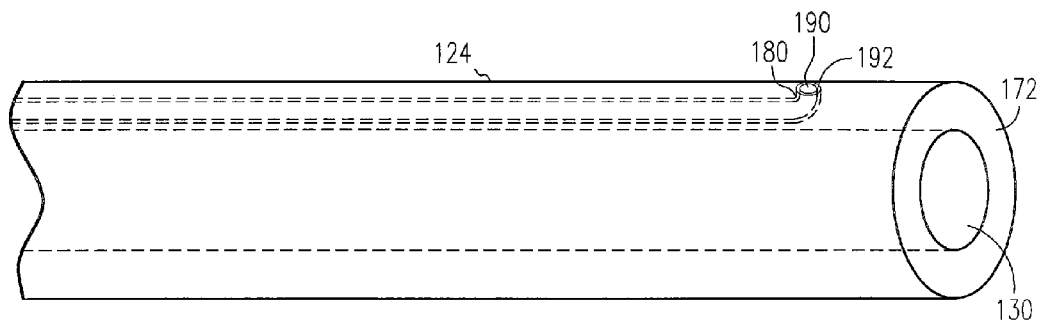
FIG. 9 is a perspective view illustrating a proximal end portion of a catheter body constructed in accordance with one embodiment.

In another embodiment, as shown in FIGS. 8 and 9, the catheter assembly 100" further includes an accessory lumen 190. It should be noted that the embodiments shown in FIGS. 8 and 9 can be incorporated with any of the above-discussed embodiments. The accessory lumen 190 is disposed adjacent to the delivery lumen 130, and in one option, the accessory lumen 190 has a substantially smaller diameter than the delivery lumen 130. The delivery lumen 130, as discussed above, extends from a location in the distal end surface 170 through the proximal tip 172. The accessory lumen 190 extends from a location, in one option, in the distal tip 170 to a location 180 not in the proximal tip 172, for example, terminating at a location on the side wall 124 of the catheter body 110.

In another option, a liner 192 is disposed within the accessory lumen 190. The liner 192 includes, but is not limited to, the materials discussed above for the actuator lumen. In yet another option, a stiffening member, such as a braided member, is disposed adjacent to, or surrounding the accessory lumen 190, which assists in preventing the accessory lumen 190 from collapsing. The accessory lumen 190 is sized to receive therein accessories 194. For instance, a fiber optic instrument is disposed within the accessory lumen 190. The fiber optic instrument can be used to assist in directing the distal end of the catheter body 110 within the patient. This allows for a reduction or elimination of radiation exposure, for example, radiation exposure that occurs during fluoroscopic procedures. Other types of instruments can be disposed in the accessory lumen 190 as well, for example, an instrument 194 can includes one or more sensors 196 thereon.

To form the catheter assembly 100", the delivery lumen liner is placed over a mandrel, and the optional actuator lumen liner is optionally threaded over the pull wire and placed over the delivery lumen liner. The pull wire anchor is placed over the delivery lumen liner and coupled with the pull wire. An instrument, such as an instrument with a sensor or an instrument such as a fiber optic instrument is placed over the delivery lumen liner. Stiffening material is optionally placed over the delivery lumen liner, the actuator lumen liner, and the instrument. Outer tubing is placed over the delivery lumen liner, the optional actuator lumen liner, and the instrument, which will form the outer surface of the catheter body. The items are held together, for example, by placing shrink tubing thereover and heating the shrink tubing. The items are reflowed together, a process which blends the material of the outer tubing, actuator lumen liner, the instrument, and the delivery lumen liner. The shrink tubing is removed from the assembly.

To form the proximal end of the catheter assembly, an outer jacket is slid over a proximal end of the delivery lumen liner, but not over the actuator lumen liner nor the instrument. The outer jacket abuts the first outer jacket discussed above, and the items are secured together, for example, by heat shrink tubing. These elements are reflowed together, and the shrink tubing is removed. The deflectable catheter body assembly is coupled with a handle assembly with a steering mechanism to form the deflectable catheter assembly.

Advantageously, the deflectable catheter assembly provides a catheter assembly that is easy to use and manipulate, and does not interfere with the physician's ability to manipulate the deflectable catheter assembly. Furthermore, the catheter assembly design assists in preventing leakage from the actuator lumen and/or the accessory lumen. The catheter assembly further prevents co-mingling of fluids from the delivery lumen to the actuator lumen and/or the accessory lumen, and prevents fluids from entering the actuator lumen and/or the accessory lumen. The accessory lumen and/or the accessory lumen provide for more flexibility during implant procedures, and provides for more options with the catheter assembly.

It is to be understood that the above description is intended to be illustrative, and not restrictive. Many other embodiments will be apparent to those of skill in the art upon reading and understanding the above description. It should be noted that embodiments discussed in different portions of the description or referred to in different drawings can be combined to form additional embodiments of the present invention. Furthermore, although a deflectable catheter assembly has been discussed throughout, it should be understood that the actuator lumen and the accessory lumen, and the various combinations discussed and/or shown in the application can be incorporated within other types of catheter assemblies, including, but not limited to, radiopaque catheter assemblies, non-deflectable catheter assemblies or slittable catheter assemblies, or slittable catheter assemblies, or catheter assemblies removable in any fashion from instruments disposed therein. The scope of the invention should, therefore, be determined with reference to the appended claims, along with the full scope of equivalents to which such claims are entitled.

What is claimed is:

1. A deflectable catheter assembly comprising:
   a catheter body extending from a deflectable distal end to a proximal end and having an intermediate portion therebetween;
   the catheter body including an actuator lumen and a delivery lumen;
   the delivery lumen extending from the deflectable distal end through the proximal end;
   the actuator lumen extending from a position near the deflectable distal end to the intermediate portion and not through the proximal end; the actuator lumen exiting the catheter body forming an exit lumen on a side wall of the catheter body; and
   a liner, wherein at least a portion of the liner extends toward the proximal end from the exit lumen and is outside of the catheter body, and the liner is sealed around the exit lumen, and a lumen extends through the liner and through at least a portion of the actuator lumen.

2. The deflectable catheter assembly as recited in claim 1, further comprising a pull wire disposed within the actuator lumen, the pull wire coupled with the catheter body near the deflectable distal end.

3. The deflectable catheter assembly as recited in claim 2, wherein the pull wire exits through the exit lumen.

4. The deflectable catheter assembly as recited in claim 1, further comprising a liner disposed within the actuator lumen.

5. The deflectable catheter assembly as recited in claim 1, further comprising a means for deflecting the deflectable distal end.

6. The deflectable catheter assembly as recited in claim 1, further comprising a delivery lumen liner disposed within the delivery lumen.

7. The deflectable catheter assembly as recited in claim 1, wherein the catheter body is slittable without damage to an instrument disposed therein.

8. The deflectable catheter assembly as recited in claim 1, further comprising a stiffening member coupled with the liner.

9. The deflectable catheter assembly as recited in claim 1, wherein the liner is formed of PTFE.

10. The deflectable catheter assembly as recited in claim 1, wherein a proximal tip of the catheter body does not have a lumen coupled with the actuator lumen.

11. The deflectable catheter assembly as recited in claim 1, further comprising a medical instrument disposed through the delivery lumen.

12. The deflectable catheter assembly as recited in claim 1, wherein the liner is sealed around the exit lumen with reflowed material disposed around the liner.

13. The deflectable catheter assembly as recited in claim 1, wherein the catheter body has an accessory lumen therein, the accessory lumen extending from a position near the deflectable distal end and terminating in the intermediate portion, and the accessory lumen does not continuously extend from the deflectable distal end to the proximal end.

14. The deflectable catheter assembly as recited in claim 1, wherein the catheter body has an accessory lumen therein, the accessory lumen extending from a position near the deflectable distal end and terminating in the intermediate portion, and the accessory lumen does not continuously extend from the deflectable distal end to the proximal end.

* * * * *